United States Patent

Gesing et al.

Patent Number: 4,902,689
Date of Patent: Feb. 20, 1990

[54] INSECTICIDAL 1,2,3,4-TETRAHYDRO-5-NITRO-PYRIMIDINE DERIVATIVES

[75] Inventors: Ernst R. Gesing, Erkrath-Hochdahl; Hilmar Wolf, Langenfeld; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[21] Appl. No.: 271,551

[22] Filed: Nov. 15, 1988

[30] Foreign Application Priority Data

Nov. 18, 1987 [DE] Fed. Rep. of Germany ....... 3739263

[51] Int. Cl.$^4$ .................... C07D 487/04; A01N 43/90
[52] U.S. Cl. ................................... 514/258; 544/281; 544/280; 544/279
[58] Field of Search ............... 544/282, 279, 280, 281; 514/258

[56] References Cited

FOREIGN PATENT DOCUMENTS 3638121 12/1987 Fed. Rep. of Germany .

Primary Examiner—Mukund J. Shah
Assistant Examiner—C. L. Cseh
Attorney, Agent, or Firm—Sprung, Horn, Kramer & Woods

[57] ABSTRACT

Insecticidal 1,2,3,4-tetrahydro-5-nitropyrimidines of the formula

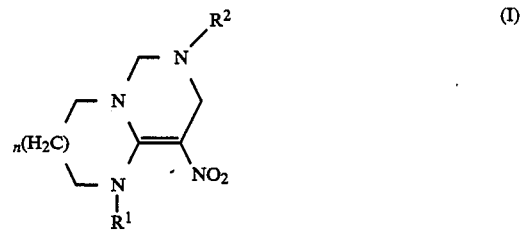

in which
R$^1$ stands for hydrogen or for optionally substituted radicals from the group consisting of benzyl, picolyl (pyridylmethyl) and phenoxyalkyl,
n stands for the number 0 or 1 and
R$^2$ stands for the —A—R$^3$ group, in which
A stands for a direct bond or for the —(CH$_2$)$_m$— or —(CH$_2$)$_x$—Y—(CH$_2$)$_z$— groupings, where
m stands for the numbers 1 to 4,
x and z stand for the numbers 0, 1 or 2, it being possible for x and z to be identical or different, and
Y stands for oxygen, sulphur or for the —NH— or $$-\underset{\underset{R^4}{|}}{CH}- \text{ groupings,}$$

groupings,
where
R$^4$ stands for optionally alkoxycarbonyl-substituted C$_1$-C$_4$-alkyl, cyano, hydroxyl or for phenyl, and
R$^3$ stands for halogeno-C$_1$-C$_4$-alkyl or for an optionally substituted radical selected from the group consisting of phenyl, naphthyl, anthryl, phenanthryl, pyridyl, furyl, thienyl, piperidyl and 1,3-benzodioxolyl, with certain exceptions,
and salts thereof.

12 Claims, No Drawings

INSECTICIDAL 1,2,3,4-TETRAHYDRO-5-NITRO-PYRIMIDINE DERIVATIVES

The present invention relates to new 1,2,3,4-tetrahydro-5-nitro-pyrimidine derivaties, a process for their preparation and their use in pesticides, in particular as insecticides.

It has already been disclosed that certain pyrimidinothiazines such as, for example, 7-ethyl-9-nitro-3,4,7,8-tetrahydro-(2H,6H)-pyrimidino-[4,3-b]-1,3-thiazine, exhibit insecticidal properties (cf. (U.S. Pat. No. 4,031,087).

The new 1,2,3,4-tetrahydro-5-nitro-pyrimidine derivatives of the formula (I)

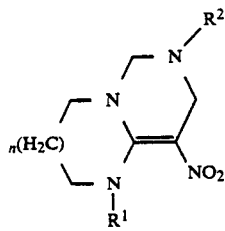

in which (a)

$R^1$ stands for hydrogen or for optional substituted radicals from the series comprising benzyl, picolyl (pyridylmethyl) and phenoxyalkyl, n stands for the number 0 or 1 and $R^2$ stands for the —A—$R^3$ group, in which A stands for a direct bond or for the —(CH$_2$)$_m$— or —(CH$_2$)$_x$—Y—(CH$_2$)$_z$— groupings, where
m stands for the numbers 1 to 4,
x and z stand for the numbers 0, 1 or 2, it being possible for x and z to be identical or different,
and
Y stands for oxygen, sulphur or for the —NH— or

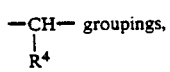 groupings, where $R^4$ stands for optionally alkoxycarbonyl-substituted $C_1$-$C_4$-alkyl, cyano, hydroxyl or for phenyl, and $R^3$ stands for optionally substituted radicals from the series comprising phenyl, naphthyl, anthryl, phenanthryl, pyridyl, furyl, thienyl, piperidyl or 1,3-benzodioxolyl, with the exception of the compounds (a), in which (α) $R^1$ stands for the 2-chloro-pyridin-5-yl-methyl radical and $R^2$ simultaneously stands for the following radicals: benzyl, 4-chlorobenzyl, 2-chlorobenzyl, pyridin-3-yl-methyl, furan-2-yl-methyl, phenethyl, thien-2-yl-methyl, 1-phenyl-ethyl and 3,4-dimethoxybenzyl, or (β) $R^1$ stands for hydrogen and simultaneously $R^2$ denotes benzyl, pyridin-3-yl-methyl and 4-chlorobenzyl, or in which $R^1$ stands for hydrogen or for optionally substituted radicals from the series comprising benzyl, picolyl and phenoxyalkyl, n stands for the number 0 or 1 and $R^2$ stands for the —A—$R^3$ group, in which A stands for a direct bond or for the —(CH$_2$)$_m$— or —(CH$_2$)$_x$—Y—(CH$_2$)$_z$— groupings, where m stands for the numbers 1 to 4, x and z stand for the numbers 0, 1 or 2, it being possible for x and z to be identical or different, and Y stands for oxygen, sulphur or for the —NH— or

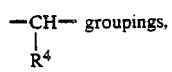 groupings, where $R^4$ stands for optionally alkoxycarbonyl-substituted $C_1$-$C_4$-alkyl, cyano, hydroxyl or for phenyl, and $R^3$ stands for halogeno-$C_1$-$C_4$-alkyl or for optionally substituted radicals from the series comprising phenyl, naphthyl, anthryl, phenanthryl, pyridyl, furyl, thienyl, piperidyl or 1,3-benzodioxolyl, and acid addition salts thereof, have been found.

Some of the new 1,2,3,4-tetrahydro-5-nitro-pyrimidine derivatves of the formula (I) possess an asymmetrically substituted carbon atom and can therefore be obtained in the two optical isomer forms. The invention relates both to the isomer mixtures and to the individual isomers.

Furthermore, it has been found that the 1,2,3,4-tetrahydro-5-nitro-pyrimidine derivatives of the formula (I) and the acid addition salts thereof are obtained when nitromethylene derivatives of the formula (II)

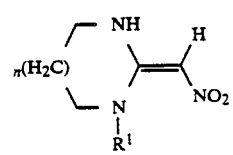

in which $R^1$ and n have the abovementioned meaning are reacted with amines of the formula (III)

$$R^3\text{—}A\text{—}NH_2 \qquad (III)$$

in which $R^3$ and A have the abovementioned meanings, in the presence of at least twice the molar amount of formaldehyde, if appropriate in the presence of acid catalysts and if appropriate in the presence of diluents, and when, if appropriate, the compounds obtained are subjected to an addition reaction with physiologically acceptable acids.

Surprisingly, the 1,2,3,4-tetrahydro-5-nitropyrimidine derivatives of the formula (I) according to the invention are distinguished as insecticides of high activity.

In the preferred and particularly preferred ranges below, the compounds which have already been excluded in the main definition are again excluded.

The invention preferably relates to compounds of the formula (I) in which (A)

n stands for the number 0,

R¹ stands for hydrogen or for radicals from the series comprising benzyl, picolyl and phenoxy-$C_1$-$C_3$-alkyl, which are optionally monosubstituted, disubstituted or trisubstituted by identical or different substituents from the series comprising halogen and/or cyano, R² stands for the —A—R³ group, in which
A stands for —$(CH_2)_x$—Y—$(CH_2)_z$— groupings,
where
m stands for the numbers 1 to 4,
x and z stand for the numbers 0, 1 or 2, it being possible for x and z to be identical or different, and
Y stands for oxygen, sulphur or for the —NH— or —CH— groupings,
|
R⁴ where
R⁴ stands for optionally $C_1$-$C_4$-alkoxycarbonyl-substituted $C_1$-$C_4$-alkyl, cyano, hydroxyl or for phenyl, and
R³ stands for radicals from the series comprising phenyl, naphthyl, anthryl, phenanthryl, pyridyl, furyl, thienyl, piperidyl or 1,3-benzodioxolyl, which are optionally monosubstituted to pentasubstituted by identical or different substituents, substituents which may be mentioned being: halogen, $C_1$-$C_4$-alkyl, halogeno-$C_1$-$C_2$-alkyl, $C_1$-$C_2$-alkoxy, halogeno-$C_1$-$C_2$-alkylthio, hydroxyl, di-$C_1$-$C_2$-alkylamino, carboxyl and phenyl.

(B) In addition, preferred compounds of the formula (I) are those in which
n stands for the number 1,
R¹ stands for hydrogen or for radicals from the series comprising benzyl, picolyl and phenoxy-$C_1$-$C_3$-alkyl, which are optionally monosubstituted, disubstituted or trisubstituted by identical or different substituents from the series comprising halogen and/or cyano, R² stands for the —A—R³ group, in which
A stands for —$(CH_2)_x$—Y—$(CH_2)_z$— groupings,
where
m stands for the numbers 1 to 4,
x and z stand for the numbers 0, 1 or 2, it being possible for x and z to be identical or different, and
Y stands for oxygen, sulphur or for the —NH— or —CH— groupings,
|
R⁴ where
R⁴ stands for optionally $C_1$-$C_4$-alkoxycarbonyl-substituted $C_1$-$C_4$-alkyl, cyano, hydroxyl or for phenyl, and
R³ stands for halogeno-$C_1$-$C_3$-alkyl or for radicals from the series comprising phenyl, naphthyl, anthryl, phenanthryl, pyridyl, furyl, thienyl, piperidyl or 1,3-benzodioxolyl, which are optionally monosubstituted to pentasubstituted by identical or different substituents, substituents which may be mentioned being: halogen, $C_1$-$C_4$-alkyl, halogeno-$C_1$-$C_2$-alkyl, $C_1$-$C_2$-alkoxy, halogeno-$C_1$-$C_2$-alkylthio, hydroxyl, di-$C_1$-$C_2$-alkylamino, carboxyl and phenyl.

Particularly preferred compounds of the formula (I) are those in which
n stands for the number 0,
R¹ stands for hydrogen or for radicals from the series comprising benzyl, picolyl and phenoxy-$C_1$-$C_2$-alkyl, which are optionally monosubstituted or disubstituted by identical or different substituents from the series comprising fluorine, chlorine, bromine and/or cyano, and R² stands for the —A—R³ group, in which
A stands for —$(CH_2)_x$—Y—$(CH_2)_z$— groupings,
where
m stands for the numbers 1 to 4,
x and z stand for the numbers 0, 1 or 2, it being possible for x and z to be identical or different, and
Y stands for oxygen, sulphur or for the —NH— or —CH— groupings,
|
R⁴ where
R⁴ stands for optionally $C_1$-$C_2$-alkoxycarbonyl-substituted $C_1$-$C_2$-alkyl, cyano, hydroxyl or for phenyl, and
R³ stands for radicals from the series comprising phenyl, naphthyl, anthryl, phenanthryl, pyridyl, furyl, thienyl, piperidyl or 1,3-benzodioxolyl, which are optionally monosubstituted to pentasubstituted by identical or different substituents, substituents which may be mentioned being: fluorine, chlorine, bromine, methyl, ethyl, n- or i-propyl, tert.-butyl, trifluoromethyl, methoxy, ethoxy, trifluoromethylthio, hydroxyl, dimethylamino, diethylamino, carboxyl and phenyl.

In addition, particularly preferred compounds of the formula (I) are those in which
n stands for the number 1,
R¹ stands for hydrogen or for radicals from the series comprising benzyl, picolyl and phenoxy-$C_1$-$C_2$-alkyl, which are optionally monosubstituted or disubstituted by identical or different substituents from the series comprising fluorine, chlorine, bromine and/or cyano, and R² stands for the —A—R³ group, in which
A stands for —$(CH_2)_x$—Y—$(CH_2)_z$— groupings,
where
m stands for the numbers 1 to 4,
x and z stand for the numbers 0, 1 or 2, it being possible for x and z to be identical or different, and
Y stands for oxygen, sulphur or for the —NH— or —CH— groupings,
|
R⁴ where
R⁴ stands for optionally $C_1$-$C_2$-alkoxycarbonyl-substituted $C_1$-$C_2$-alkyl, cyano, hydroxyl or for phenyl, and
R³ stands for halogeno-$C_1$-$C_2$-alkyl and for radicals from the series comprising phenyl, naphthyl, anthryl, phenanthryl, pyridyl, furyl, thienyl, piperidyl or 1,3-benzodioxolyl, which are optionally monosubstituted to pentasubstituted by identical or different substituents, substituents which may be mentioned being: fluorine, chlorine, bromine, methyl, ethyl, n- or i-propyl, tert.-butyl, trifluoromethyl, methoxy, ethoxy, trifluoromethylthio, hydroxyl, dimethylamino, diethylamino, carboxyl and phenyl.

Other preferred compounds according to the invention are addition products of acids and those 1,2,3,4-tetrahydro-5-nitro-pyrimidine derivatives of the formula (I) in which the substituents R, $R^1$, $R^2$ or the index n have the meanings which have already preferably been mentioned for these substituents and the index.

The acids which can be adducted preferably include hydrohalic acids, such as, for example, hydrochloric acid and hydrobromic acid, in particular hydrochloric acid, furthermore phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, phthalic acid, naphthalenesulphonic acid, nicotinic acid, citric acid and ascorbic acid.

If, for example, 3-(2-chloro-pyridin-5-yl-methyl)-2-nitro-methylene-imidazolidine, 4-fluorobenzylamine and at least twice the molar amount of formaldehyde are employed as starting substances in the process according to the invention, the corresponding reaction may be represented by the following equation:

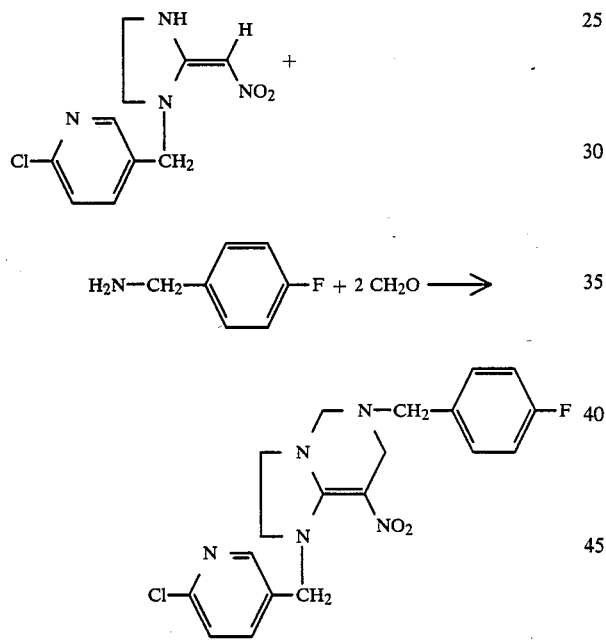

Formula (II) provides a general definition of the nitromethylene derivatives to be employed as starting substances in the process according to the invention. In this formula (II), $R^1$ and n preferably stand for those radicals which have already preferably been mentioned for this substituent and the index n in connection with the description of the substances of the formula (I) according to the invention.

The compounds of the formula (II) are known and/or can be prepared by known methods (cf. for example DE-OS (German Published Specification) No. 2,514,402, EP-OS (European Published Specification) No. 136,636, EP-OS (European Published Specification) No. 154,178 and EP-OS (European Published Specification) No. 163,855).

Formula (III) provides a general definition of the amines also to be employed as starting substances in the process according to the invention. In this formula (III), $R^3$ and A preferably stand for those radicals which have already preferably been mentioned for these substituents in connection with the description of the substances of the formula (I) according to the invention.

The amines of the formula (III) are generally known compounds of organic chemistry.

Examples which may be mentioned of the compounds of the formula (III) are:

$$R^3-A-NH_2 \quad (III)$$

TABLE 1

| A | $R^3$ |
|---|---|
| $-\overset{CH_3}{\underset{\phantom{X}}{CH}}-$ | 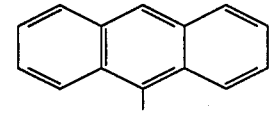 |
| $-\overset{CH_3}{\underset{\phantom{X}}{CH}}-$ | 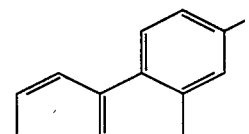 |
| $-\overset{CH_3}{\underset{\phantom{X}}{CH}}-$ | 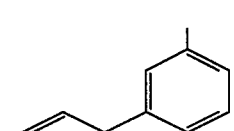 |
| $-\overset{CH_3}{\underset{\phantom{X}}{CH}}-$ | 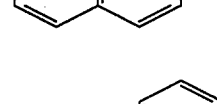 |
| $-CH_2-$ | 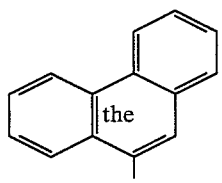 |
| $-CH_2-$ | 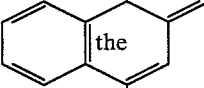 |
| $-CH_2-$ | 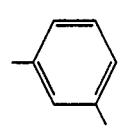 |
| $-CH_2-$ |  |

TABLE 1-continued

| A | R³ |
|---|---|
| —CH₂— | 3,4,5-trimethoxyphenyl |
| —CH₂— | 4-(trifluoromethyl)phenyl |
| —CH₂— | 4-carboxyphenyl |
| —CH₂— | 3,5-dimethylphenyl |
| —CH₂— | 1-naphthyl |
| —CH₂—CH₂— | 2-methoxyphenyl |
| —CH₂—CH₂— | 3-methoxyphenyl |
| —CH₂—CH₂— | 4-methoxyphenyl |
| —CH₂—CH₂— | 3,4-dimethoxyphenyl |
| —CH₂—CH₂— | 4-hydroxyphenyl |
| —CH₂—CH₂— | 3,4-dihydroxyphenyl |
| —CH₂—CH₂— | 3-(trifluoromethyl)phenyl |
| —CH(OH)—CH₂— | phenyl |
| —(CH₂)₃— | phenyl |
| —CH(CH₃)—(CH₂)₂— | phenyl |
| —(CH₂)₄— | phenyl |
| —(CH₂)₂—CH(C₆H₅)— | phenyl |
| —CH(C₆H₅)—CH₂— | 4-methylphenyl |
| —CH(CH₃)— | 3-(N,N-dimethylamino)phenyl |
| —CH(C₆H₅)—CH₂— | piperidin-1-yl |
| —CH(CN)— | pentafluorophenyl |
| —CH(CN)— | 3-(trifluoromethylthio)phenyl |

TABLE 1-continued

| A | R³ |
|---|---|
| 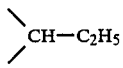 | 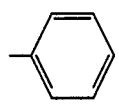 |
| 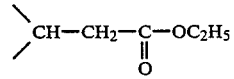 | 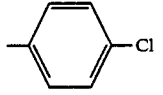 |
| 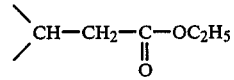 | 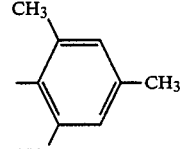 |
|  | 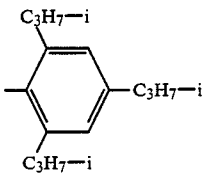 |

The process according to the invention for preparing the new compounds of the formula (I) is preferably carried out using diluents. Suitable diluents here are water, and, for the reaction, inert organic solvents. These preferably include aliphatic and aromatic optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, alcohols, such as methanol, ethanol, n-propanol and isopropanol. Mixtures of alcohols and water are preferably employed.

If appropriate, the process according to the invention is carried out in the presence of acid, non-oxidizing catalysts. Catalysts which have proved particularly successful are hydrohalic acids, such as hydrochloric acid and hydrobromic acid, phosphoric acid, and lower carboxylic acids, such as acetic acid and propionic acid.

When carrying out the process according to the invention, the reaction temperatures can be varied within a relatively wide range. In general, the process is carried out at temperatures between −20° C. and +120° C., preferably at temperatures between 0° C. and +80° C.

The process according to the invention is generally carried out under atmospheric pressure. However, it is also possible to carry out the process under increased or reduced pressure.

For carrying out the process according to the invention, 1 to 1.5 moles, preferably 1 to 1.2 moles, of amine of the formula (III) and 2 to 4 moles, preferably 2 to 3 moles, of formaldehyde are employed per mole of nitromethylene derivative of the formula (II).

If appropriate, the amines of the formula (III) can be employed in the form of aqueous solutions. If gaseous amines of the formula (III) are used, these compounds can be passed through the mixture of diluent, compounds of the formula (II) and formaldehyde. In the process according to the invention, an aqueous solution of formaldehyde is employed. In general, the reactions are carried out in a suitable diluent, and the reaction mixture is stirred for several hours at the specifically required temperature. In the process according to the invention, working up is carried out in each case by customary methods.

The acid addition salts of the compounds of the formula (I) can be obtained in a simple manner by customary salt formation methods, for example by dissolving a compound of the formula (I) in a suitable inert solvent and adding the acid, for example, hydrochloric acid, and isolated in a known manner, for example by filtering off, and, if necessary, purified by washing using an inert organic solvent.

The active compounds are suitable for combating animal pests, in particular insects, and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus-differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesmaquadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Psudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix hurberiella, Phyllocnistis-citrella,* Agrotis spp., Euxoa spp., Feltia spp., *Earias insulana,* Heliothis spp., *Spodcptera exigua, Mamestra brassicae, Panolis flammea, Prodenia litura,* Spodoptera spp., *Trichoplusia*

*ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chyrysocephala, Epilachna varivestis,* Atomaria spp. *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor* Agriotes spp., Conoderus spp., *Melolontha melonontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterbra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.*

The active compounds of the formula (I) according to the invention are distinguished by an excellent insecticidal activity. In particular when applied as leaf-insecticides and soil-insecticides, they show excellent action against grubs, such as, for example, *Phorbia antiqua* grubs against caterpillars, such as, for example, *Plutella maculipennis,* against beetle larvae, such as, for example, *Phaedon cochleariae* and *Diabrotica balteata,* and aphids, such as, for example, *Myzus persicae* and *Aphis fabae.*

The new compounds are thus particularly suitable for use in combating leaf insects and soil insects.

Furthermore, the new compounds show a bactericidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl suphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, midges, ticks, etc., in the sectors of animal keeping and cattle breeding; better results, for example higher milk production, greater weight, more attractive animal pelt, longer life, etc., can be achieved by combating the pests.

In particular when employed as ectoparasiticides, they show an excellent action against blowfly larvae, such as, for example, *Lucilia cuprina*.

The application of the active compounds according to the invention in this sector is carried out in known manner, such as by external application in the form of, for example, dipping, spraying, pouring-on, spotting-on and dusting.

The biological effectiveness of the compounds according to the invention will be explained with reference to the examples below.

PREPARATION EXAMPLE

EXAMPLE 1

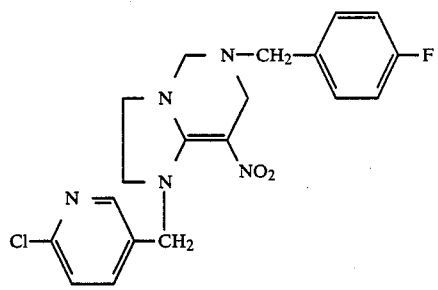

1.5 ml (0.02 mole) of 37% strength aqueous formaldehyde solution are added dropwise and at room temperature to a mixture of 2.54 g (0.01 mole) of 3-(2-chloropyridin-5-yl-methyl)-2-nitromethylene-imidazolidine and 1.25 g (0.01 mole) of 4-fluorobenzylamine in 90 ml of ethanol, and the mixture is heated under reflux for 3 hours. The mixture is cooled to room temperature, the solvent is removed in vacuo, and ether is added to the residue, which is filtered off with suction.

3.41 g (78% of theory) of 6,7-dihydro-6-(4-fluorobenzyl)-8-nitro-(5H)-3-(2-chloropyridin-5-yl-methyl)-imidazolidino-[2,3f]-pyrimidine of melting point 159° C. are obtained.

The compounds of the formula (I) indicated in the following Table 2 can be prepared in analogy to Example 1 or the process according to the invention:

TABLE 2

| Ex. No. | n | $R^1$ | $R^2$ | Physical constant |
|---|---|---|---|---|
| 2 | 1 | —CH$_2$—(2-chloropyridin-5-yl) | —CH$_2$—(3-fluorophenyl) | m.p.: 156° C. |
| 3 | 0 | —CH$_2$—(2-chloropyridin-5-yl) | —CH$_2$—(2,3-dichlorophenyl) | m.p.: 168° C. |
| 4 | 0 | —CH$_2$—(2-chloropyridin-5-yl) | —CH$_2$—(4-methylphenyl) | m.p.: 146° C. |
| 5 | 0 | —CH$_2$—(2-chloropyridin-5-yl) | —CH$_2$—(pyridyl) | m.p.: 150° C. |

TABLE 2-continued
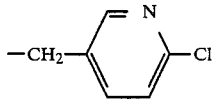
(I)
| Ex. No. | n | R¹ | R² | Physical constant |
|---|---|---|---|---|
| 6 | 0 | 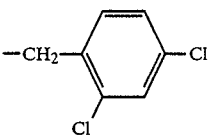 | 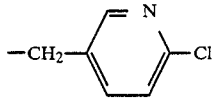 | m.p.: 139° C. |
| 7 | 0 | 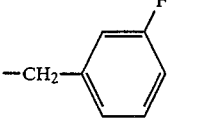 | 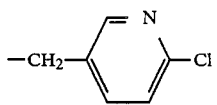 | m.p.: 124° C. |
| 8 | 0 | 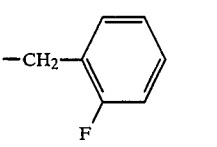 | 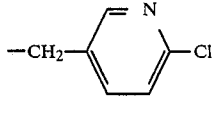 | m.p.: |
| 9 | 1 | 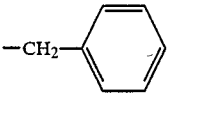 | 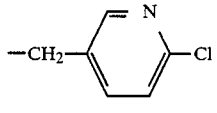 | m.p.: 99° C. |
| 10 | 1 | 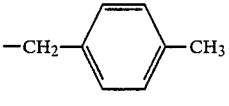 | 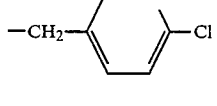 | m.p.: 132° C. |
| 11 | 1 | 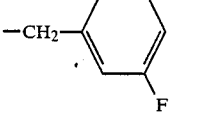 | 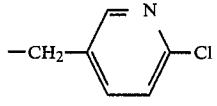 | m.p.: 146° C. |
| 12 | 1 | 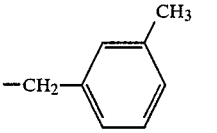 | 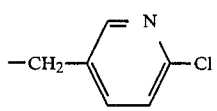 | m.p.: 135° C. |
| 13 | 1 | 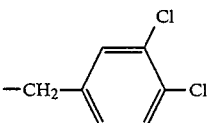 | 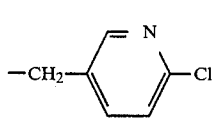 | m.p.: 149° C. |
| 14 | 1 | 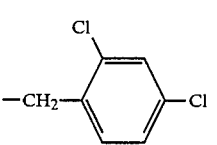 | | m.p.: 91° C. |

TABLE 2-continued (I) Structure: A six-membered ring containing two N atoms (bearing R¹ and R²-CH₂ groups) connected via CH₂ groups to a central N; the ring bears =C(NO₂)– and –N(R¹)– substituents; n(H₂C) bridge.

| Ex. No. | n | R¹ | R² | Physical constant |
|---|---|---|---|---|
| 15 | 1 | –CH₂-(6-chloro-pyridin-3-yl) | –CH₂-(2-methoxyphenyl) | m.p.: 154° C. |
| 16 | 1 | –CH₂-(6-chloro-pyridin-3-yl) | –CH₂-(4-chlorophenyl) | m.p.: 78° C. |
| 17 | 1 | –CH₂-(6-chloro-pyridin-3-yl) | –CH₂-(3,4-difluorophenyl) | m.p.: 142° C. |
| 18 | 0 | –CH₂-(6-chloro-pyridin-3-yl) | –CH₂-(2,5-difluorophenyl) | m.p.: 42° C. |
| 19 | 1 | –CH₂-(6-chloro-pyridin-3-yl) | –CH₂-(2,5-difluorophenyl) | m.p.: 118° C. |
| 20 | 1 | –CH₂-(6-chloro-pyridin-3-yl) | –CH₂-(pyridin-2-yl) | m.p.: 60° C. |
| 21 | 1 | –CH₂-(6-chloro-pyridin-3-yl) | –CH₂-(4-fluorophenyl) | m.p.: 144° C. |
| 22 | 1 | –CH₂-(6-chloro-pyridin-3-yl) | –CH₂-(3-chlorophenyl) | m.p.: 135° C. |
| 23 | 0 | –CH₂-(6-chloro-pyridin-3-yl) | –CH₂-(6-chloro-pyridin-3-yl) | m.p.: 156° C. |

TABLE 2-continued
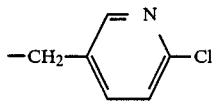
(I)
| Ex. No. | n | R¹ | R² | Physical constant |
|---|---|---|---|---|
| 24 | 1 | 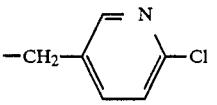 | 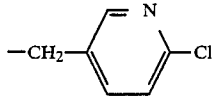 | m.p.: 124° C. |
| 25 | 1 | 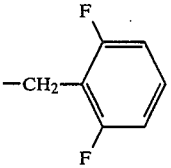 | 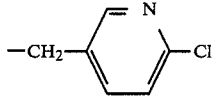 | m.p.: 143° C. |
| 26 | 0 | 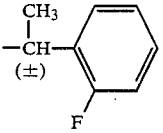 | 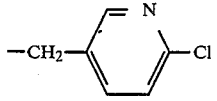 | m.p.: 81° C. |
| 27 | 1 | 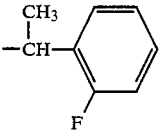 | 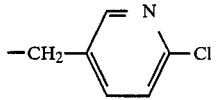 | m.p.: 127° C. |
| 28 | 0 | 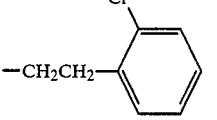 | 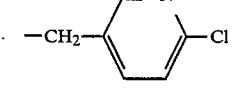 | m.p.: 166° C. |
| 29 | 1 | 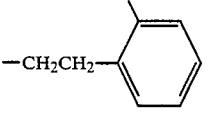 | 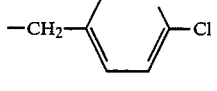 | m.p.: 141° C. |
| 30 | 1 | 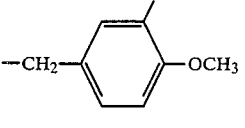 | 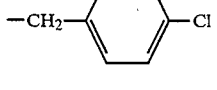 | m.p.: 185° C. |
| 31 | 0 | 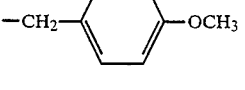 | 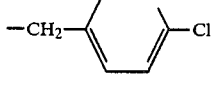 | m.p.: 166° C. |
| 32 | 1 | 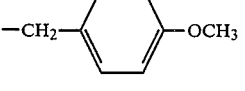 | | m.p.: 149° C. |

TABLE 2-continued
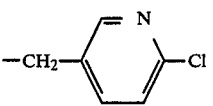
(I)
| Ex. No. | n | R¹ | R² | Physical constant |
|---|---|---|---|---|
| 33 | 0 | 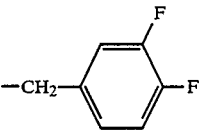 | 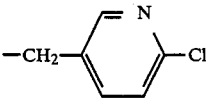 | m.p.: 129° C. |
| 34 | 0 | 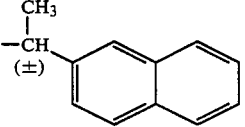 | 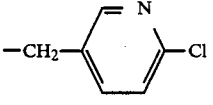 | m.p.: 91° C. |
| 35 | 1 | 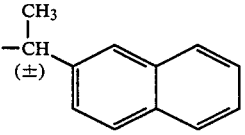 | 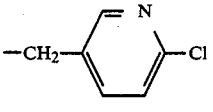 | Oil |
| 36 | 0 | 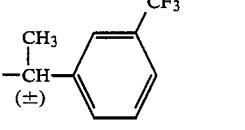 | 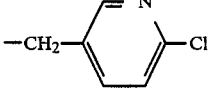 | m.p.: 88° C. |
| 37 | 1 | 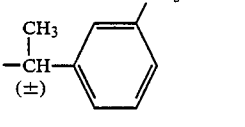 | 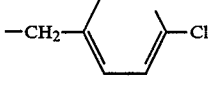 | m.p.: 68° C. |
| 38 | 0 | 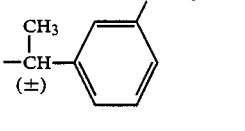 | 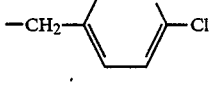 | m.p.: 121° C. |
| 39 | 1 | 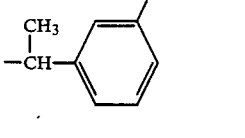 | 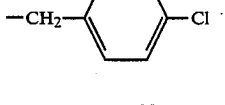 | Oil |
| 40 | 0 | 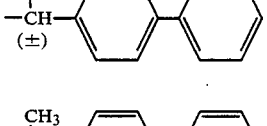 | 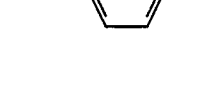 | m.p.: 190° C. |
| 41 | 1 | 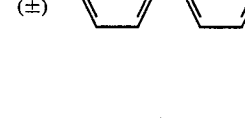 | | m.p.: 109° C. |

TABLE 2-continued

Structure (I): A seven-membered ring containing N-R¹, C(=C(NO₂)-)-, N-, CH₂-N(R²)-CH₂, with (CH₂)ₙ bridge.

| Ex. No. | n | R¹ | R² | Physical constant |
|---|---|---|---|---|
| 42 | 0 | —CH₂-(2-chloropyridin-5-yl) | —CH₂-(2,6-difluorophenyl) | m.p.: 151° C. |
| 43 | 1 | —CH₂-(2-chloropyridin-5-yl) | —CH₂CH₂-(4-chlorophenyl) | m.p.: 94° C. |
| 44 | 1 | —CH₂-(2-chloropyridin-5-yl) | —CH₂CH₂—S—CH₂-(2,6-dichlorophenyl) | m.p.: 87° C. |
| 45 | 1 | —CH₂-(2-chloropyridin-5-yl) | —CH(CH₃)-(naphthalen-2-yl), S(—) | m.p.: 153° C. |
| 46 | 1 | —CH₂-(2-chloropyridin-5-yl) | —CH(CH₃)-phenyl, S(—) | m.p.: 87° C. |
| 47 | 1 | —CH₂-(2-chloropyridin-5-yl) | —CH(CH₃)-phenyl, (±) | m.p.: 168° C. |
| 48 | 0 | —CH₂-(2-chloropyridin-5-yl) | —CH₂-(2-methoxyphenyl) | m.p.: 122° C. |
| 49 | 0 | —CH₂-(2-chloropyridin-5-yl) | —CH(CH₃)-(3-bromophenyl) | m.p.: 116° C. |
| 50 | 1 | —CH₂-(2-chloropyridin-5-yl) | —CH(CH₃)-(3-bromophenyl), (±) | m.p.: 127° C. |

TABLE 2-continued
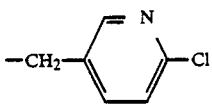
(I)
| Ex. No. | n | R¹ | R² | Physical constant |
|---|---|---|---|---|
| 51 | 0 | 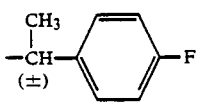 | 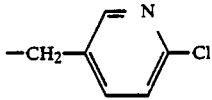 | m.p.: 132° C. |
| 52 | 1 | 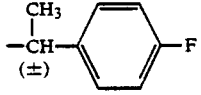 | 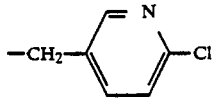 | m.p.: 170° C. |
| 53 | 0 | 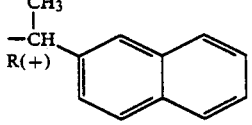 | 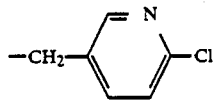 | m.p.: 103° C. |
| 54 | 1 | 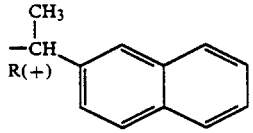 | 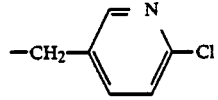 | m.p.: 147° C. |
| 55 | 0 | 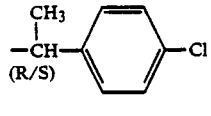 | 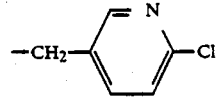 | m.p.: 123° C. |
| 56 | 1 | 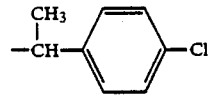 | 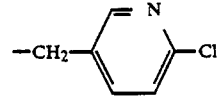 | m.p.: 129° C. |
| 57 | 1 | 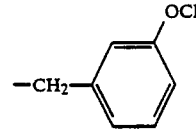 | 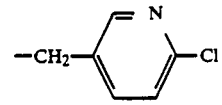 | m.p.: 146° C. |
| 58 | 0 | 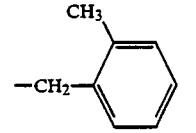 | 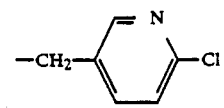 | m.p.: 129° C. |
| 59 | 0 | 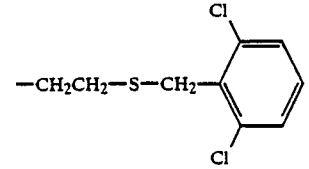 | 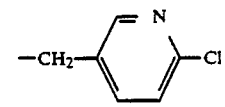 | m.p.: 136° C. |
| 60 | 1 | 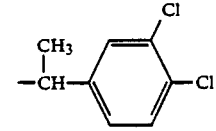 | | m.p.: 137° C. |

TABLE 2-continued

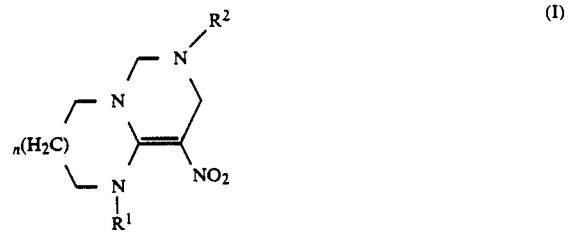

| Ex. No. | n | R¹ | R² | Physical constant |
|---|---|---|---|---|
| 61 | 1 | -CH₂-(2-chloropyridin-5-yl) | -CH₂-(2-methylphenyl) | m.p.: 68° C. |
| 62 | 0 | -CH₂-(2-chloropyridin-5-yl) | -CH₂-CH₂-phenyl (phenethyl, with extra phenyl) | m.p.: 157° C. |
| 63 | 1 | -CH₂-(2-chloropyridin-5-yl) | -CH(phenyl)-CH₂-phenyl | Oil |
| 64 | 0 | -CH₂-(2-chloropyridin-5-yl) | -CH₂-CH(phenyl)₂ | m.p.: 199° C. |
| 65 | 1 | -CH₂-(2-chloropyridin-5-yl) | -CH₂-CH(phenyl)₂ | m.p.: 94° C. |
| 66 | 0 | -CH₂-(2-chloropyridin-5-yl) | S(−)-CH(CH₃)-(naphthalen-2-yl) | m.p.: 67° C. |
| 67 | 1 | -CH₂-(2-chloropyridin-5-yl) | -CH₂-(thiophen-2-yl) | m.p.: 129° C. |
| 68 | 1 | -CH₂-(2-chloropyridin-5-yl) | -CH₂-(furan-2-yl) | m.p.: 132° C. |

TABLE 2-continued

Structure (I):

Piperazine-type ring with $_n(H_2C)$ bridge, substituents $R^1$ on N and $R^2$ on N, with =C-NO$_2$ group.

| Ex. No. | n | R¹ | R² | Physical constant |
|---|---|---|---|---|
| 69 | 1 | −CH₂−(6-chloropyridin-3-yl) | −CH(CH₃)−(4-bromophenyl) (R/S) | m.p.: 157° C. |
| 70 | 1 | −CH₂−(6-chloropyridin-3-yl) | −CH(CH₃)−(2-methoxyphenyl) | m.p.: 132° C. |
| 71 | 0 | −CH₂−(6-chloropyridin-3-yl) | −CH(CH₃)−(2-methoxyphenyl) | m.p.: 111° C. |
| 72 | 0 | −CH₂−(6-chloropyridin-3-yl) | −CH(CH₃)−(4-bromophenyl) (±) | m.p.: 118° C. |
| 73 | 0 | −CH₂−(6-chloropyridin-3-yl) | −CH₂CH₂−(4-chlorophenyl) | m.p.: 146° C. |
| 74 | 0 | −CH₂−(6-chloropyridin-3-yl) | −CH(CH₃)−(4-methylphenyl) | m.p.: 139° C. |
| 75 | 0 | −CH₂−(6-chloropyridin-3-yl) | −CH(CH₃)−(4-methylphenyl) | m.p.: 132° C. |
| 76 | 0 | −CH₂−(6-chloropyridin-3-yl) | −CH(CH₃)−(3,4-dichlorophenyl) | m.p.: 121° C. |
| 77 | 0 | −CH₂−(6-chloropyridin-3-yl) | −CH₂−(3-methoxyphenyl) | m.p.: 128° C. |
| 78 | 0 | −CH₂−(6-chloropyridin-3-yl) | −CH(CH₃)−(4-bromophenyl) (−) | m.p.: 157° C. |

TABLE 2-continued (I) Structure: cyclic compound with N-R², N, N-R¹, =NO₂, and n(H₂C) bridge.

| Ex. No. | n | R¹ | R² | Physical constant |
|---|---|---|---|---|
| 79 | 0 | —CH₂—(2-chloropyridin-5-yl) | —CH(CH₃)—C₆H₄—Br (4-Br) (+) | m.p.: 164° C. |
| 80 | 1 | —CH₂—(2-chloropyridin-5-yl) | —CH₂CH₂—O—CH₂—CF₃ | m.p.: 77° C. |
| 81 | 0 | —CH₂—(2-chloropyridin-5-yl) | —CH(CH₃)—C₆H₄—Cl (4-Cl) (−) | m.p.: 159° C. |
| 82 | 0 | —CH₂—(2-chloropyridin-5-yl) | —CH(CH₃)—C₆H₄—Cl (4-Cl) (+) | m.p.: 154° C. |
| 83 | 1 | —CH₂—(2-chloropyridin-5-yl) | —CH(CH₃)—C₆H₄—Cl (4-Cl) (+) | Oil |
| 84 | 0 | —CH₂—(2-chloropyridin-5-yl) | —CH₂—(2,4-difluorophenyl) (R/S) | m.p.: 138° C. |
| 85 | 1 | —CH₂—(2-chloropyridin-5-yl) | —CH₂—(2,4-difluorophenyl) | m.p.: 166° C. |
| 86 | 0 | —CH₂—(2-chloropyridin-5-yl) | —CH(CH₃)—(2,4-dichlorophenyl) (±) | m.p.: 174° C. |
| 87 | 0 | —CH₂—(2-chloropyridin-5-yl) | —CH₂—(3-methylphenyl) | m.p.: 124° C. |
| 88 | 0 | —CH₂—(2-chloropyridin-5-yl) | —C₆H₅ | m.p.: 189° C. |

TABLE 2-continued (I) [structure: bicyclic system with $R^1$, $R^2$, $n(H_2C)$, $NO_2$]

| Ex. No. | n | $R^1$ | $R^2$ | Physical constant |
|---|---|---|---|---|
| 89 | 0 | $-CH_2-$(2-chloropyridin-5-yl) | $-$(4-F-phenyl) | m.p.: 121° C. |
| 90 | 0 | $-CH_2-$(2-chloropyridin-5-yl) | $-$(4-$OCF_3$-phenyl) | m.p.: 182° C. |
| 91 | 0 | $-CH_2-$(2-chloropyridin-5-yl) | $-$(4-Cl-phenyl) | m.p.: 193° C. |
| 92 | 0 | H | $-CH(CH_3)$-phenyl (±) | m.p.: 155° C. |
| 93 | 1 | H | $-CH(CH_3)$-phenyl (±) | m.p.: 149° C. |
| 94 | 0 | $-CH_2-$(2-CN-phenyl) | $-CH_2-$(pyridin-3-yl) | m.p.: 180° C. |
| 95 | 0 | $-CH_2CH_2-O-$(4-Cl-phenyl) | $-CH_2CH_2NHCH_2-$phenyl | Oil |
| 96 | 0 | $-CH_2CH_2-O-$(4-Br-phenyl) | $-CH_2-$(pyridin-3-yl) | Oil |
| 97 | 0 | $-CH_2CH_2-O-$(4-Cl-phenyl) | $-CH_2-$(pyridin-3-yl) | Oil |

Use Examples

In the use examples below, the following compound was employed as comparison substance:

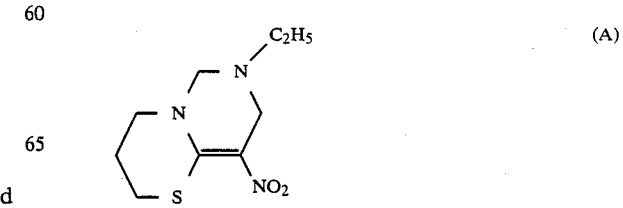

(A)

7-Ethyl-9-nitro-3,4,7,8-tetrahydro-(2H,6H)-pyrimidino-[4,3-b]-1,3-thiazine from U.S. Pat. No. 4,031,087.

EXAMPLE A

Phaedon larvae test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the compounds of Preparation Examples 8, 87, 2, 16, 13, 14, 15, 12, 11, 10, 21, 22, 23, 24, 9, 20, 33, 17, 18, 31, 32, 30, 28, 29, 42, 25, 26, 27, 38, 39, 40, 41, 36, 37, 49, 50, 34, 35, 46, 47, 48, 59, 43, 44, 45, 58, 57, 55, 56, 53, 54, 66, 68, 51, 52, 62, 65, 72, 69, 70, 71, 86, 84, 85, 82, 83, 81, 80, 79, 78, 3, 4, 5, 6, 7 and 1 show superior activity compared with the prior art.

EXAMPLE B

Aphis test (systemic action)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which are heavily infested with the black bean aphid (*Aphis fabae*) are treated by being dipped into the preparation of the active compound in the desired concentration.

After the specified periods of time, the destruction in % is determined. 100% means that all the aphids have been killed; 0% means that none of the aphids have been killed.

In this test, for example, the compounds of Preparation Examples 8, 87, 30, 28, 42, 26, 38, 49, 59, 66, 69, 70, 71, 84, 82, 79, 3, 4, 5, 6, 7 and 1 show superior activity compared with the prior art.

EXAMPLE C

Critical concentration test/root-systemic action
Test insect: *Myzus persicae*
Solvent: 3 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds of Preparation Examples 4, 7, 8 and 87 show superior action compared with the prior art.

EXAMPLE D

Critical concentration test/soil insects
Test insect: *Phaedon cochleariae* larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Example 4, 7, 8 and 87 show superior action compared with the prior art.

EXAMPLE E

Critical concentration test/soil insects
Test insect: *Phorbia antiqua* grubs (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects The degree of effectiveness is 100% if all the test insects have been killed and is 0% if just as many test insects are still alive as in the case of the untreated control.

In this test, for example, the compound of Preparation Example 8 shows superior activity compared with the prior art.

EXAMPLE F

Critical concentration test/soil insects
Test insect: *Diabrotica balteata* larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm ($=$mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Examples 4, 7, 8 and 87 show superior activity compared with the prior art.

It will be appreciated that the instant specification and claims are set forth by way of illustration and not limitation, and that various modifications and changes may be made without departing from the spirit and scope of the present invention.

What is claimed is:

1. A 1,2,3,4-tetrahydro-5-nitropyrimidine derivative of the formula

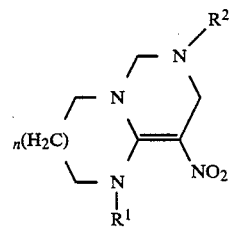

(I)

in which
(a) $R^1$ stands for hydrogen or for optionally substituted radicals from the group consisting of benzyl, picolyl (pyridylmethyl) and phenoxyalkyl, the optional substituents being selected from the group consisting of halogen and cyano,
n stands for the number 0 or 1 and
$R^2$ stands for the —A—$R^3$ group, in which
A stands for a direct bond or for the —(CH$_2$)$_m$— or —(CH$_2$)$_x$—Y—(CH$_2$)$_z$— groupings,
where
m stands for the numbers 1 to 4, x and z stand for the numbers 0, 1 or 2, it being possible for x and z to be identical or different, and
Y stands for oxygen, sulphur or for the —NH— or

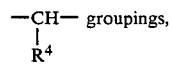

where
$R^4$ stands for optionally alkoxycarbonyl-substituted $C_1$–$C_4$-alkyl, cyano, hydroxyl or for phenyl, and
$R^3$ stands for an optionally substituted radical selected from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$–$C_4$-alkyl, halogeno-$C_1$–$C_2$-alkyl, $C_1$–$C_2$-alkoxy, halogeno-$C_1$–$C_2$-alkylthio, hydroxyl, di-$C_1$–$C_2$-alkylamino, carboxyl and phenyl, with the exception of the compounds (a), in which
(α) $R^1$ stands for the 2-chloro-pyridin-5-yl-methyl radical and
$R^2$ simultaneously stands for benzyl, 4-chlorobenzyl, 2-chlorobenzyl, pyridin-3-yl-methyl, furan-2-yl-methyl, phenethyl, thien-2-yl-methyl, 1-phenylethyl or 3,4-dimethoxybenzyl, or
(β) $R^1$ stands for hydrogen and simultaneously $R^2$ denotes benzyl, pyridin-3-yl-methyl and 4-chlorobenzyl, or in which
(b) $R^1$ stands for hydrogen or for optionally substituted radicals from the group consisting of benzyl, picolyl and phenoxyalkyl, the optional substituents being selected from the group consisting of halogen and cyano,
n stands for the number 0 or 1 and
$R^2$ stands for the —A—$R^3$ group, in which
A stands for a direct bond or for the —(CH$_2$)$_m$— or —(CH$_2$)$_x$—Y—(CH$_2$)$_z$— groupings, where
m stands for the numbers 1 to 4,
x and z stand for the numers 0, 1 or 2, it being possible for x and z to be identical or different, and
Y stands for oxygen, sulphur or for the —NH— or

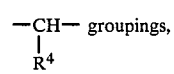

where
$R^4$ stands for optionally alkoxycarbonyl-substituted $C_1$–$C_4$-alkyl, cyano, hydroxyl or for phenyl, and
$R^3$ stands for halogeno-$C_1$–$C_4$-alkyl or for an optionally substituted radicals from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$–$C_4$-alkyl, halogeno-$C_1$–$C_2$-alkyl, $C_1$–$C_2$-alkoxy, halogeno-$C_1$–$C_2$-alkylthio, hydroxyl, di-$C_1$–$C_2$-alkylamino, carboxyl and phenyl, or an addition salt thereof.

2. A 1,2,3,4-tetrahydro-5-nitropyrimidine derivative or salt thereof according to claim 1, in which
n stands for the number 0,
$R^1$ stands for hydrogen or for a radical from the group consisting of benzyl, picolyl and phenoxy-$C_1$–$C_3$-alkyl which is optionally monosubstituted, disubstituted or trisubstituted by identical or different substituents from the group consisting of halogen and cyano, $R^2$ stands for the —A—$R^3$ group, in which A —$(CH_2)_m$— or —$(CH_2)_x$—Y—$(CH_2)_z$— groupings, where m stands for the numbers 1 to 4, x and z stand for the numbers 0, 1 or 2, it being possible for x and z to be identical or different, and Y stands for oxygen, sulphur or for the —NH— or $$-\underset{R^4}{\overset{|}{CH}}-\text{ groupings,}$$

where $R^4$ stands for optionally $C_1$-$C_4$-alkoxycarbonyl-substituted $C_1$-$C_4$-alkyl, cyano, hydroxyl or for phenyl, and $R^3$ stands for an optionally substituted radical selected from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$-$C_4$-alkyl, halogeno-$C_1$-$C_2$-alkyl, $C_1$-$C_2$-alkoxy, halogeno-$C_1$-$C_2$-alkylthio, hydroxyl, di-$C_1$-$C_2$-alkylamino, carboxyl and phenyl.

3. A 1,2,3,4-tetrahydro-5-nitro-pyrimidine derivative or salt thereof according to claim 1, n stands for the number 1, $R^1$ stands for hydrogen or for a radical selected from the group consisting of benzyl, picolyl and phenoxy-$C_1$-$C_3$-alkyl, each of which is optionally monosubstituted, disubstituted or trisubstituted by identical or different substituents from the group consisting of halogen and cyano, $R^2$ stands for the —A—$R^3$ group, in which A stands for the —$(CH_2)_m$— or —$(CH_2)_x$—Y—$(CH_2)_z$— groupings, where m stands for the numbers 1 to 4, x and z stand for the numbers 0, 1 or 2, it being possible for x and z to be identical or different, and Y stands for oxygen, sulphur or for the —NH— or $$-\underset{R^4}{\overset{|}{CH}}-\text{ groupings,}$$

where $R^4$ stands for optionally $C_1$-$C_4$-alkoxycarbonyl-substituted $C_1$-$C_4$-alkyl, cyano, hydroxyl or for phenyl, and $R^3$ stands for halogeno-$C_1$-$C_3$-alkyl or for an optionally substituted radical selected from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$-$C_4$-alkyl, halogeno-$C_1$-$C_2$-alkyl, $C_1$-$C_2$-alkoxy, halogeno-$C_1$-$C_2$-alkylthie, hydroxyl, di-$C_1$-$C_2$-alkylamino, carboxyl and phenyl.

4. A 1,2,3,4-tetrahydro-4-nitro-pyrimidine derivative or salt thereof according to claim 1, in which n stands for the number 0, $R^1$ stands for hydrogen or for a radical selected from the group consisting of benzyl, picolyl and phenoxy-$C_1$-$C_2$-alkyl, which are optionally monosubstituted or disubstituted by identical or different substituents from the group consisting of fluorine, chlorine, bromine and cyano, and $R^2$ stands for the —A—$R^3$ group, in which A stands for the —$(CH_2)$— or —$(CH_2)_x$—Y—$(CH_2)_z$— groupings, where m stands for the numbers 1 to 4, x and z stand for the numbers 0, 1 or 2, it being possible for x and z to be identical or different, and Y stands for oxygen, sulphur or for the —NH— or $$-\underset{R^4}{\overset{|}{CH}}-\text{ groupings,}$$

where $R^4$ stands for optionally $C_1$-$C_2$-alkoxycarbonyl-substituted $C_1$-$C_2$-alkyl, cyano, hydroxyl or for phenyl, and $R^3$ stands for an optionally substituted radical selected from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$-$C_4$-alkyl, halogeno-$C_1$-$C_2$-alkyl, $C_1$-$C_2$-alkoxy, halogeno-$C_1$-$C_2$-alkylthie, hydroxyl, di-$C_1$-$C_2$-alkylamino, carboxyl and phenyl.

5. A 1,2,3,4-tetrahydro-5-nitro-pyrimidine derivative or salt thereof according to claim 1, n stands for the number 1, $R^1$ stands for hydrogen or for a radical from the group consisting of benzyl, picolyl and phenoxy-$C_1$-$C_2$-alkyl, which are optionally monosubstituted or disubstituted by identical or different substituents from the the group consisting of fluorine, chlorine, bromine and cyano, and $R^2$ stands for the —A—$R^3$ group, in which A $m$ —$(CH_2)_x$—Y—$(CH_2)_z$— groupings, where m stands for the numbers 1 to 4, x and z stand for the numbers 0, 1 or 2, it being possible for x and z to be identical or different, and Y stands for oxygen, sulphur or for the —NH— or $$-\underset{R^4}{\overset{|}{CH}}-\text{ groupings,}$$

where $R^4$ stands for optionally $C_1$-$C_2$-alkoxycarbonyl-substituted $C_1$-$C_2$-alkyl, cyano, hydroxyl or for phenyl, and $R^3$ stands for halogeno-$C_1$-$C_2$-alkyl and for an optionally substituted radical from the group consisting of phenyl, naphthyl, anthryl, phenanthryl, pyridyl, furyl, thienyl, piperidyl and 1,3-benzodioxolyl, the optional substituents being selected from the group consisting of halogen, $C_1$-$C_4$-alkyl, halogeno-$C_1$-$C_2$-alkyl, $C_1$-$C_2$-alkoxy, halogeno-$C_1$-$C_2$-alkylthio, hydroxyl, di-$C_1$-$C_2$-alkylamino, carboxyl and phenyl.

6. A compound according to claim 1, wherein such compound is 6,7-dihydro-6-(4-methyl-benzyl)-8-nitro-(5H)-3-(2-chloropyridin-5-yl-methyl)-imidazolidino[2,3-f]-pyrimidine of the formula

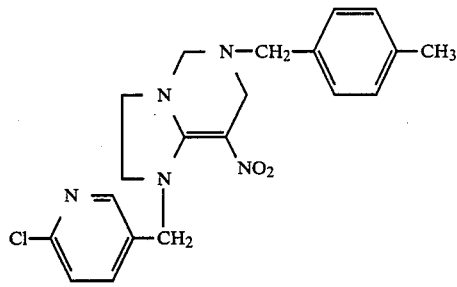

or an acid addition salt thereof.

7. A compound according to claim 1, wherein such compound is 6,7-dihydro-6-(3-fluoro-benzyl)-8-nitro-(5H)-3-(2-chloropyridin-5-yl-methyl)-imidazolidino-[2,3-f]-pyrimidine of the formula

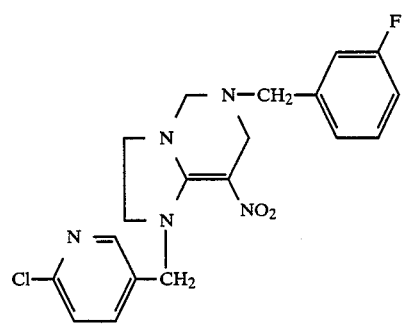

or an acid addition salt thereof.

8. A compound according to claim 1, wherein such compound is 6,7-dihydro-6-(2-fluoro-benzyl)-8-nitro-(5H)-3-(2-chloropyridin-5-yl-methyl)-imidazolidino-[2,3-f]-pyrimidine of the formula

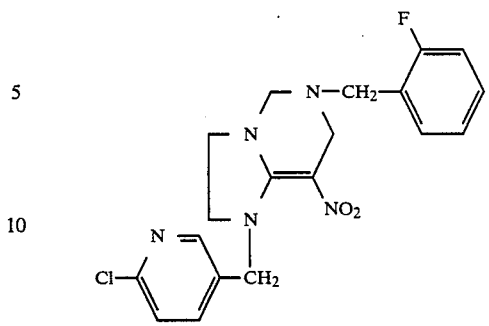

or an acid addition salt thereof.

9. A compound according to claim 1, wherein such compound is 6,7-dihydro-6-(3-methyl-benzyl)-8-nitro-(5H)-3-(2-chloropyridin-5-yl-methyl)-imidazolidino-[2,3-f]-pyrimidine of the formula or an acid addition salt thereof.

10. An insecticidal composition comprising an insecticidally effective amount of a compound or salt thereof according to claim 1 and a diluent.

11. A method of combating insects which comprises applying to such insects or to an insect habitat an insecticidally effective amount of a compound or salt thereof according to claim 1.

12. The method according to claim 11, wherein such compound is
6,7-dihydro-6-(4-methyl-benzyl)-8-nitro-(5H)-3-(2-chloropyridin-5-yl-methyl)-imidazolidino-[2,3-f]-pyrimidine,
6,7-dihydro-6-(3-fluoro-benzyl)-8-nitro-(5H)-3-(2-chloropyridin-5-yl-methyl)-imidazolidino-[2,3-f]-pyrimidine,
6,7-dihydro-6-(2-fluoro-benzyl)-8-nitro-(5H)-3-(2-chloropyridin-5-yl-methyl)-imidazolidino-[2,3-f]-pyrimidine, or
6,7-dihydro-6-(3-methyl-benzyl)-8-nitro-(5H)-3-(2-chloropyridin-5-yl-methyl)-imidazolidino-[2,3-f]-pyrimidine,
or an addition salt thereof.

UNITED STATES PATENT AND TRADEMARK OFFICE
CERTIFICATE OF CORRECTION

PATENT NO. : 4,902,689

DATED : February 20, 1990

INVENTOR(S) : Ernst R. Gesing, et al

It is certified that error appears in the above-identified patent and that said Letters Patent is hereby corrected as shown below:

Title Page, Abstract, line 10 from bottom: Delete "groupings"

Col. 39, line 3: After "A" insert --stands for the $-CH_2)_m-$ or --

Col. 39, line 28: After "1," insert --in which--

Col. 39, line 62: Before "nitro" delete "-4-" and substitute -- -5- --

Col. 40, line 4: After "$-(CH_2)$" insert --$_m$--

Col. 40, line 30: After "1," insert --in which--

Col. 40, line 40: After "A" delete "$_m$" and insert --stands for the $-(CH_2)_m-$ or --

Signed and Sealed this

Sixteenth Day of June, 1992

Attest:

DOUGLAS B. COMER

*Attesting Officer*   *Acting Commissioner of Patents and Trademarks*